United States Patent [19]

DeFusco et al.

[11] Patent Number: 4,775,729

[45] Date of Patent: Oct. 4, 1988

[54] CURABLE POLYETHER COMPOSITIONS

[75] Inventors: Albert A. DeFusco, Cumberland, Md.; Eugene C. Martin, Ridgecrest, Calif.

[73] Assignee: The United States of America as represented by the Secretary of the Navy, Washington, D.C.

[21] Appl. No.: 867,660

[22] Filed: May 23, 1986

Related U.S. Application Data

[63] Continuation-in-part of Ser. No. 710,249, Mar. 8, 1985, Pat. No. 4,675,414.

[51] Int. Cl.$^4$ ............................................. C08F 22/40
[52] U.S. Cl. ................................................... 526/262
[58] Field of Search ........................................ 526/262

[56] References Cited

U.S. PATENT DOCUMENTS

| | | | |
|---|---|---|---|
| 3,729,446 | 4/1976 | Holub et al. | 260/47 CZ |
| 3,951,888 | 4/1976 | Isayama et al. | 525/404 |
| 3,959,391 | 5/1976 | Allain | 260/615 B |
| 4,124,657 | 11/1978 | Martin et al. | 526/49 |
| 4,156,761 | 5/1979 | Martin et al. | 526/52.5 |
| 4,215,046 | 7/1980 | Martin et al. | 260/326.26 |

Primary Examiner—C. Warren Ivy
Assistant Examiner—Alex H. Walker
Attorney, Agent, or Firm—William C. Townsend; Stephen J. Church

[57] ABSTRACT

Pentadienyl ether terminated polyethers and maleimidomethyl carbonate terminated polyethers are selectively combined via a Diels-Alder reaction at room temperature. The resulting aliphatic copolyethers are characterized by having at least two chemically combined N(1)-oxycarbonyloxymethyl-4-oxymethyltetrahydrophthalimido groups interposed between polyether radicals within the copolymer chain. The aliphatic polyether precursors terminated with pentadienyl ether groups are synthesized by reacting an aliphatic hydroxy terminated polyether with a metal alkoxide to form at least the bis alkoxide derivative. The alkoxide derivative is then reacted with a halogen substituted pentadiene yielding the bis or tris pentadiene ether terminated polyether for use in the copolymer synthesis.

8 Claims, No Drawings

CURABLE POLYETHER COMPOSITIONS

CROSS-REFERENCES TO RELATED APPLICATIONS

This application is a continuation-in-part of Ser. No. 710,249 of the invention entitled Maleimidomethyl-Carbonate Polyethers, filed on Mar. 8, 1985 by Albert DeFusco et al U.S. Pat. No. 4,675,414.

BACKGROUND OF THE INVENTION

1. Field of the Invention

This invention relates to room temperature curable aliphatic copolyethers. More specifically, it relates to aliphatic copolyethers derived from the one-step reaction of a pentadienyl ether terminated polyether and a maleimidomethyl carbonate terminated polyether.

2. Description of the Prior Art

The reaction of hydroxyl terminated polybutadiene with napthyl-potassium in successive steps to form the bis(1,3-pentadienyl ether) derivative is known in the chemical art. The resulting pentadienyl ether terminated polymers are cured at room temperature via a Diels-Alder reaction. The cure takes place upon addition of a curing agent, the bisdieneophile bismaleimide of dimer diamine.

Preparation of imido-substituted polyester compositions wherein phosgene, carbonates and diols may be used as linking agents is known in the chemical art. These imido-substituted polycarbonates are cured at a temperature between 50° C. and 300° C. Mixtures of the imido-substituted polycarbonates and other organic polymers are possible, however, these blends require free radical initiators and a temperature between 50° C. and 300° C. for curing.

Likewise, the preparation of bisalkyl unsaturated polyalkylene oxide through a standard Williamson synthesis is well known. A polyalkylene oxide having allyl end-groups was prepared by subjecting an alkylene oxide monomer to addition polymerization in the presence of potassium oxide and then reacting the polymerized alkylene oxide with an allyl halide compound. Alternatively, a polymerized alkylene oxide was reacted with an organic polyhalide and with an allyl halide compound in successive steps in order to achieve a polyalkylene oxide of greater molecular weight having allyl end-groups. Both the polymerization and the reactions with the organic polyhalide and allyl halide were carried out at a temperature selected from the range of 20° C. to 100° C.

SUMMARY OF THE INVENTION

According to the present invention, aliphatic copolyethers are synthesized having at least two chemically combined N(1)-oxycarbonyloxymethyl-4-oxymethyltetrahydrophthalimido groups of the formula:

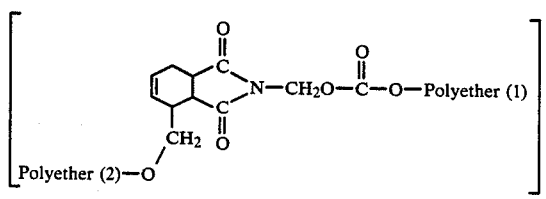

wherein Polyether (1) is the residue from a bis methyl maleimide terminated aliphatic polyether precursor and wherein polyether (2) is the residue from a bis pentadienyl ether terminated polyether precursor.

Martin et al., in U.S. Pat. Nos. 4,215,046 and 4,124,657, incorporated herein by reference, disclose the reaction of a bis(1,3-pentadienyl ether) terminated polybutadiene with a curing agent, the bisdieneophile bismaleimide of dimer diamine. The room temperature cured elastomer is the result of a Diels-Alder reaction between the conjugated diene polybutadiene prepolymer and the curing agent which is a bisdieneophile. The present invention eliminates the curing agent by using two separate polyether precursors which are terminated with end-groups that participate in a Diels-Alder reaction. The present invention utilizes pentadienyl ether terminated polyethers and maleimidomethyl carbonate terminated polyethers as product precursors which are combined via a Diels-Alder reaction in a one step synthesis to form the aliphatic copolyethers.

The aliphatic pentadienyl ether terminated polyethers used as product precursors are synthesized by an improved Williamson synthesis comprising a two-step reaction at room temperature and atmospheric pressure. First, sodium or potassium hydride is used to generate the metal alkoxide of the aliphatic hydroxyl terminated polyether. Next, the metal alkoxide is reacted with a halogen substituted pentadiene to form the aliphatic pentadienyl ether terminated polyether.

The aliphatic copolyethers of the present invention may be used as binders for explosives and propellants.

OBJECTS OF THE INVENTION

An object of this invention is the one-step synthesis via a Diels-Alder reaction at room temperature of the novel aliphatic copolyether copolymers of the invention.

Another object is to provide novel aliphatic copolyethers distinguished by the presence of N(1)-oxycarbonyloxymethyl-4-oxymethyltetrahydrophthalimido groups linking the polyether radicals within the polymer.

Yet another object of this invention is the use of pentadienyl ether terminated polyethers prepared by an improved two-step Williamson synthesis as product precursors in the synthesis of the aliphatic copolyether copolymers described herein.

Other objects, advantages and novel features of the invention will become apparent from the following description.

DETAILED DESCRIPTION OF THE INVENTION

In the present invention pentadienyl ether terminated polyethers and maleimidomethyl carbonate terminated polyethers are selectively combined via a Diels-Alder reaction at room temperature. The resulting aliphatic copolyethers are characterized by having at least two chemically combined N(1)-oxycarbonyloxymethyl-4-oxymethyltetrahydro-phthalimido groups of the formula:

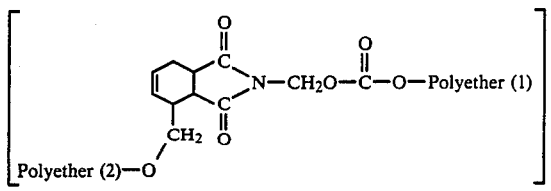

wherein polyether (1) is the residue from a bis methyl maleimide terminated aliphatic polyether precursor and wherein polyether (2) is the residue from a bis pentadienyl ether terminated polyether precursor.

The aliphatic polyether polymer precursors terminated with pentadienyl ether groups are synthesized by reacting an aliphatic hydroxy terminated polyether with a metal alkoxide to form at least the bis alkoxide derivative. The alkoxides are then alkylated utilizing a halogen substituted pentadiene to form the bis or tris diene ether terminated aliphatic polyethers.

The metal alkoxide used in this synthesis route may be sodium or potassium hydride. In addition, naphthyl potassium may be used to generate the potassium alkoxide of the aliphatic hydroxyl terminated polymer. The halogen substituted pentadiene utilized in the synthesis may be selected from the group consisting of iodo, chloro, and bromo 2,4-pentadiene; e.g. 1-bromo-2,4-pentadiene.

Among the polyethers which may be used in the synthesis are the polyoxyalkyl derivatives of glycols and triols such as 1,4-butanediol, 1,4-cyclohexanediol, glycerine, 1,2,6-hexanetriol, trimethylolpropane and pentaerythritol. Other polyethers include the polyoxyalkylene derivatives of glycols and triols such as propylene glycol, diethylene glycol, ethylene glycol, triethylene glycol, 1,3-butylene glycol and 1,4-butylene glycol. The polyoxyalkyl derivatives of bisphenols, halogenated bisphenols, polytetrahydrofurans and isomers of dihydroxybenzeneacetic acid may also be used.

The maleimide terminated aliphatic polyether precursors are synthesized under mild conditions and in two efficient steps from corresponding hydroxyl terminated polyethers. The polyethers can be produced by reaction between a hydroxyl terminated aliphatic polyether and phosgene (carbonyl chloride) to form the intermediate chloroformate. The chloroformate is then reacted with N-hydroxymethylmaleimide yielding an aliphatic hydroxyl terminated polyether having at least two chemically combined methylmaleimide groups of the formula:

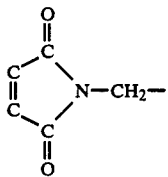

joined directly to the polyether by a carbonate linkage.

Polyethers including the saturated polyoxyalkyl derivatives and the polyoxyalkylene derivatives of the glycols and triols as disclosed above for the synthesis of the pentadienyl ether terminated aliphatic polyether precursors are also suitable for the preparation of the maleimide terminated aliphatic polyethers.

The following examples are given to illustrate the invention but should not be considered as limiting.

EXAMPLE 1

The synthesis of the product of the reaction of the bispentadienyl ether and the bismaleimidomethyl carbonate of polypropylene glycol (M.W. 425) was as follows.

The bispentadienyl ether of polypropylene glycol (M.W. 425) was prepared by introducing a solution of 8.5 grams (0.08 moles) of polypropylene glycol (M.W. 425) dropwise into a stirring suspension of 3.2 grams (0.08 moles) of sodium hydride in 10 ml of dry dioxane (or dry dimethoxyethane) under $N_2$. After 1 hour of stirring at ambient temperature, neat 1-bromo-2,4-pentadiene (11.8 grams, 0.08 moles) was added slowly at 10° C. over a 20 minute period. After stirring overnight at room temperature, the reaction mixture was filtered and the filtrate was evaporated at 5 mm Hg room temperature to yield 7.2 grams (65% yield) of the bispentadienyl ether of polypropylene glycol (M.W. 425) which is an oil and can be characterized by IR an proton NMR spectroscopy. The equivalent weight was determined to be 320 grams per mole by proton NMR spectroscopy.

A mixture of 3.6 mmoles of the bispentadienyl ether of propylene glycol (M.W. 425) (equivalent weight of 556 grams/mole as determined by proton NMR) and 3.6 mmoles of the bismaleimidomethyl carbonate (equivalent weight of 731 grams/mole as determined by proton NMR) was folded manually for 3 minutes. The mixture was then cast into a Sylgard mold previously treated with a Teflon (trademark of E. I. DuPont De Nemours & Company, Incorporated) mold release with 2 inch by 0.25 inch minidogbone shapes imbedded. The mold was then placed in a vacuum oven which was purged with $N_2$. After 36 hours at room temperature, the product of the reaction of the bispentadienyl ether of polypropylene glycol (M.W. 425) and the bismaleimidomethyl carbonate of propylene glycol (M.W. 425) was an extremely viscous fluid.

An aliquot of the mixture of copolymer precursors was analyzed by IR spectroscopy by monitoring the peak at 698 cm$^{-1}$ for the maleimide olefin. After 4 hours, 80% of the maleimide terminated starting material had disappeared due to cycloaddition with the diene terminated material. After 6 hours, no maleimide remained.

EXAMPLE 2

The bispentadienyl ether of polypropylene glycol (M.W. 425) was prepared as in Example 1.

The synthesis of the product of the bispentadienyl ether of polypropylene glycol (M.W. 425) and the tris malemimdomethyl carbonate of the polyoxyalkyl derivative of trimethylolpropane known as TPE 4542 (M.W. 4525 and available from such commercial sources as the BASF-Wyandotte Corp.) was carried out as in Example 1. The only difference was that 1.7 mmoles of the bispentadienyl ether and 1.7 mmoles of the trismalemimdomethyl carbonate (equivalent weight) was 1,779 grams/mole as determined by proton NMR) was used. The polymerized product was a tacky, soft rubber. The extent of the reaction was also determined to be the same as described in Example 1.

EXAMPLE 3

The trispentadienyl ether of the polyoxyalkyl derivative of trimethylolpropane known as TPE 4542 (M.W.

4542) was prepared in 56% yield according to the method of Example 1. The product is an oil and was purified by dissolving the crude material in a minimum amount of methanol and precipitating with water. This process does not contaminate the crude material with water after evaporation of a methanol solution of the polymer. The trispentadienyl ether of the polyoxyalkyl derivative of trimethylolpropane known as TPE 4542 (M.W. 4542) was identified by IR and proton NMR spectroscopy and has an equivalent weight of 1,425 grams/mole.

The synthesis of the product of the trispentadienyl ether of the polyoxyalkyl derivative of trimethylolpropane known as TPE 4542 (M.W. 4542) and the trismaleimidomethyl carbonate of the polyoxyalkyl derivative of trimethylolpropane known as TPE 4542 (M.W. 4542) was as described in Example 1, except that 1.4 mmoles of the trispentadienyl ether (equivalent weight of 1,426 grams/mole as determined by proton NMR) and 1.4 mmoles of the trismaleimidomethyl carbonate was used. The polymerized product is a soft and elastomeric material. The extent of the reaction was determined as in Example 1. A glass transition temperature of about −60° C. was detected by differential scanning calorimetry. The polymerized product was tested on a mechanical tester and showed a maximum stress of about 36 psi and an elongation of about 260%. The initial modulus was determined to be about 87 psi.

Obviously, many modifications and variations of the present invention are possible. It should be understood that, within the scope of the appended claims, the invention may be practiced otherwise than as specifically described.

What is claimed is:

1. A method for producing a room temperature curable aliphatic copolyether derived from the reaction between a maleimide terminated aliphatic polyether precursor and at least a bis diene ether terminated polyether comprising:
   (a) combining at least a bis methyl maleimide terminated aliphatic polyether precursor in which the methylmaleimide groups are joined directly to the polyether by a carbonate linkage with at least a bis pentadienyl ether terminated polyether precursor;
   (b) curing said precursors at room temperature via a Diels-Alder reaction between said methylmaleimide end-groups and said pentadienyl ether end-groups for a time sufficient to effect copolymerization; and
   (c) recovering said copolymerized product of said precursors.

2. As a composition of matter, the copolymerization product produced according to the method of claim 1.

3. As a composition of matter, aliphatic copolyethers having at least two chemically combined N(1)-oxycarbonyloxymethyl-4-oxymethyltetrahydrophthalimido groups of the formula:

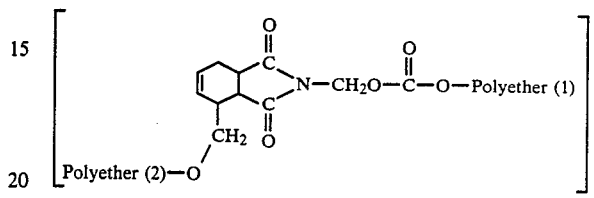

wherein Polyether (1) is the residue from a bis methyl maleimide terminated aliphatic polyether precursor and wherein Polyether (2) is the residue from a bis pentadienyl ether terminated polyether precursor.

4. As a composition of matter, the reaction product of the bispentadienyl ether and the bismaleimidomethyl carbonate of the polyoxyalkyl derivative of polypropylene glycol (M.W. 425).

5. As a composition of matter, the reaction product of the bispentadienyl ether of propylene glycol (M.W. 425) and the trismaleimidomethyl carbonate of the polyoxyalkyl derivative of trimethylolpropane (M.W. 4542).

6. As a composition of matter, the reaction product of the trispentadienyl ether of the polyoxyalkyl derivative of trimethylolpropane (M.W. 4542) and the trismaleimidomethyl carbonate of the polyoxyalkyl derivative of trimethylolpropane (M.W. 4542).

7. As a composition of matter the bispentadienyl ether of polypropylene glycol having a molecular weight of 425.

8. As a composition of matter the trispentadienyl ether of the polyoxyalkyl derivative of trimethylolpropane having a molecular weight of 4542.

* * * * *